United States Patent
Kumashiro et al.

(10) Patent No.: US 8,704,170 B2
(45) Date of Patent: Apr. 22, 2014

(54) METHOD AND APPARATUS FOR GENERATING AND ANALYZING IONS

(75) Inventors: Sumio Kumashiro, Kyoto (JP); Wenjian Sun, Shanghai (CN); Li Ding, Manchester (GB)

(73) Assignee: Shimadzu Research Laboratory (Shanghai) Co. Ltd., Shanghai (CN)

( * ) Notice: Subject to any disclaimer, the term of this patent is extended or adjusted under 35 U.S.C. 154(b) by 0 days.

(21) Appl. No.: 13/634,190

(22) PCT Filed: Apr. 22, 2011

(86) PCT No.: PCT/CN2011/073156
§ 371 (c)(1),
(2), (4) Date: Sep. 11, 2012

(87) PCT Pub. No.: WO2011/131142
PCT Pub. Date: Oct. 27, 2011

(65) Prior Publication Data
US 2013/0026359 A1    Jan. 31, 2013

(30) Foreign Application Priority Data

Apr. 22, 2010 (CN) .......................... 2010 1 0165176

(51) Int. Cl.
*H01J 49/00* (2006.01)
*H01J 49/10* (2006.01)
*H01J 49/24* (2006.01)
*H01J 49/16* (2006.01)

(52) U.S. Cl.
CPC ................ *H01J 49/10* (2013.01); *H01J 49/24* (2013.01); *H01J 49/161* (2013.01); *H01J 49/165* (2013.01); *H01J 49/164* (2013.01)
USPC .................................... 250/288; 250/423 R

(58) Field of Classification Search
CPC ......... H01J 27/02; H01J 49/10; H01J 49/161; H01J 49/165; H01J 49/26; H01J 49/105; H01J 49/164; H01J 49/24
USPC ...................... 250/281, 282, 288, 423 R, 424
See application file for complete search history.

(56) References Cited

U.S. PATENT DOCUMENTS

| | | | |
|---|---|---|---|
| 5,115,131 | A | 5/1992 | Jorgenson et al. |
| 6,211,516 | B1 | 4/2001 | Syage et al. |

(Continued)

FOREIGN PATENT DOCUMENTS

| | | |
|---|---|---|
| CN | 101206207 A | 6/2008 |
| CN | 101281165 A | 10/2008 |

(Continued)

OTHER PUBLICATIONS

Koichi Tanaka et al., Protein and Polymer Analyses up to m/z 100 000 by Laser Ionization Time-of-flight Mass Spectrometry, Rapid Communications in Mass Spectrometry, 1988, pp. 151-153, vol. 2, No. 8, Japan.

(Continued)

*Primary Examiner* — Nicole Ippolito
(74) *Attorney, Agent, or Firm* — Morris Manning & Martin LLP; Tim Tingkang Xia, Esq.

(57) ABSTRACT

The current invention involves a method and a device for generating and analyzing ions in order to analyze samples directly without sample preparation. The gaseous neutral molecules are desorbed under atmospheric pressure by a desorption method. The desorbed neutral molecules are then transferred into a low pressure region where they are postionized by a mist from an electrospray probe tip or by photons from a vacuum UV source. The generated ions are then focused in a time varying electric field in the low pressure chamber before they are transferred into a mass spectrometer or ion mobility spectrometer for further analysis.

34 Claims, 7 Drawing Sheets

(56) References Cited

U.S. PATENT DOCUMENTS

| | | | |
|---|---|---|---|
| 6,278,111 B1 | 8/2001 | Sheehan et al. | |
| 7,230,237 B2 | 6/2007 | Ueno | |
| 2005/0056766 A1* | 3/2005 | Keller | 249/120 |
| 2005/0056776 A1* | 3/2005 | Willoughby et al. | 250/281 |
| 2008/0087812 A1* | 4/2008 | Musselman | 250/285 |
| 2009/0242755 A1 | 10/2009 | Tang et al. | |
| 2010/0032059 A1 | 2/2010 | Maurici et al. | |
| 2010/0163723 A1* | 7/2010 | Shiokawa et al. | 250/282 |
| 2011/0006198 A1* | 1/2011 | Whitehouse et al. | 250/282 |
| 2011/0049352 A1 | 3/2011 | Ding et al. | |
| 2011/0220784 A1* | 9/2011 | Roach et al. | 250/282 |

FOREIGN PATENT DOCUMENTS

| | | |
|---|---|---|
| CN | 101329299 A | 12/2008 |
| CN | 101520432 A | 9/2009 |
| WO | 03031931 A2 | 4/2003 |

OTHER PUBLICATIONS

Stefan Mitschke et al., Comprehensive Gas Chromatography—Time-of-Flight Mass Spectrometry Using Soft and Selective Photoionization Techniques, Analytical Chemical, Sep. 15, 2006, pp. 6364-6375, vol. 78, No. 18, Germany.

Charles N. McEwen et al., Analysis of Solids, Liquids, and Biological Tissues Using Solids Probe Introduction at Atmospheric Pressure on Commercial LC/MS Instruments, Analytical Chemistry, Dec. 1, 2005, pp. 7826-7831, vol. 77, No. 23, Wilmington, Delaware.

Markus Haapala et al., Desorption Atmospheric Pressure Photoionization, Analytical Chemistry, Oct. 15, 2007, pp. 7867-7872, vol. 79, No. 20, Finland.

Robert B. Cody et al., Versatile New Ion Source for the Analysis of Materials in Open Air under Ambient Conditions, Analytical Chemistry, Apr. 15, 2006, pp. 2297-2302, vol. 77, No. 8, Maryland.

Zoltan Takats, et al., Mass Spectrometry Sampling Under Ambient Conditions with Desorption Electrospray Ionization, Science, Oct. 15, 2004, pp. 471-473, vol. 306.

Jentaie Shiea et al., Electrospray-assisted laser desorption/ionization mass spectrometry for direct ambient analysis of solids, Rapid Communications in Mass Spectrometry, 2005, pp. 3701-3704; vol. 19.

John B. Fenn et al., Electrospray Ionization for Mass Spectrometry of Large Biomolecules, Science, Oct. 6, 1989, pp. 64-71, vol. 246, New Haven, CT.

Jack A. Syage et al., Atmospheric pressure photoionization II. Dual source ionization, Journal of Chromatography A., 2004, pp. 137-149, vol. 1050.

Markus Marksteiner et al., UV and VUV Ionization of Organic Molecules, Cluster, and Complexes, J. Phys. Chem. A, 2009, pp. 9952-9957, vol. 113.

* cited by examiner

METHOD AND APPARATUS FOR GENERATING AND ANALYZING IONS

FIELD OF THE INVENTION

This invention relates generally to a process for generating and analyzing ions, and more particularly to a method and a device for generating and ionizing gaseous neutral molecules in a low pressure region.

BACKGROUND OF THE INVENTION

Years after mass spectrometry served as an extremely useful analytical technique in many different fields, ionization process still remains to be one of the most important techniques for meeting the increasingly demanding applications. Matrix-assisted laser desorption/ionization (MALDI, Rapid Commun. Mass Spectrom. 1988, 2, 151) and electrospray ionization (ESI, Science 1989, 246, 64) are the two techniques signifying the emergence of the mass spectrometry in wide spread biological applications. Both methods along with other mature ionization methods operated for solid or liquid require careful treatment of the sample before ionization.

Therefore, the ionization methods for rapid detection without sample pretreatment are very much desired especially in the fields of homeland security, food safety, and illicit drug detection. The invention of the desorption electrospray ionization (DESI, Science 2004, 306, 471)) started the new area of direct analysis and it greatly reduces the time needed for analyzing samples in condensed phase. Many direct analysis methods have appeared since then such as Direct Analysis in Real Time (DART, Anal. Chem. 2005, 77, 2297), atmosphere solid analysis probe (ASAP, Anal. Chem. 77, 7826), electrospray-assisted laser desorption ionization (ELDI, Rapid Commun. Mass Spectrom. 2005, 19, 3701), and desorption atmospheric pressure photoionization (DAPPI, Anal. Chem. 2007, 79, 7867). Although each method has its distinct ionization mechanism, almost all of them were operated within a two-step process. The first step involves desorbing samples from surface and forming gaseous molecules, and the second step involves ionizing the gaseous molecules and forming molecular/quasi-molecular ions.

New ionization methods have appeared with different combinations of desorption step and ionization step. Each combination features its own advantages and provides possibilities for enhanced performance in a specific area. For example, both ELDI and laser desorption photoionization (LDPI, Chinese Patent Application No. CN101520432) use laser as their desorption source, but using electrospray in the ionization step in ELDI would generate more polar species compared with those generated by a VUV lamp as ionization source in LDPI. This difference makes ELDI more adequate for analyzing biological samples whereas LDPI is more intended for being used in the field of small molecule analysis.

For almost all of direct analysis methods, both desorption and ionization process happen at the atmospheric pressure for the convenience of sample loading. The interface between the atmospheric pressure and the vacuum is responsible for the major loss of the sensitivity since the majority of ions generated cannot enter the small capillary which separates the two pressure regions. The space charge effect in the ion plume makes the spread of ions even larger, and thus fewer ions are difficult to be entrained into the gas flow entering the capillary. Additionally, a detrimental factor for introducing ions into the capillary is that the electric field at the opening of the capillary on the entrance side will inevitably defocus the ions towards the wall of the capillary and cause neutralization. Furthermore, for those ions lucky enough to enter the capillary, there is still large chance for them to lose their charges by colliding with the inner wall of the capillary.

Alternatively, if the ionization process is moved into a region after the capillary, the problem of ion loss at the interface can be alleviated. In such case, only desorbed neutral molecules will be transferred through the capillary and therefore no space charge, defocusing electric field and neutralization effects exist anymore. One of such work has been reported by Marksteiner et al. in J. Phys. Chem. A 2009, 113, 9952 involving laser desorption at atmospheric pressure and vacuum UV ionization in a TOF source in a high vacuum region. The problem of such method from the stand point of sensitivity is that only a small portion of the neutrals can reach the ionization region due to the large distance required between the interface and the ionization region to maintain a high vacuum in the TOF source. For the neutrals, no electric lens can be used to guide and focus them, and this is very harmful to sensitivity especially considering the large spread of the neutrals by the supersonic expansion right after the capillary. Although the purpose of the work by Marksteiner et al. described above is not intended for enhancing the sensitivity, it does enlighten a way of separating the two steps for direct analysis in two different pressure regions, respectively.

Similar approaches have been taken for GC coupled MS with vacuum UV as a post-ionization means. Zimmermann et al. has used an electron-beam-pumped excimer VUV lamp to photoionize effluents from a GC in the first differential pumping region of the mass spectrometer (Anal. Chem. 2006, 78, 6365-6375), which has provided lots of useful information for utilizing single photon ionization method in vacuum. Another example is as mentioned in US Patent Publication No. 2010/0032059 in which the GC effluents were photoionized at low pressure by a VUV lamp fulfilled with the inert gas.

For various ionization methods, their ionization efficiencies differ very much from different pressures. Moreover, considering the different application fields of ion sources from one to another, it is an ideal solution to operate two or more ionization methods simultaneously while testing a complex mixture. Therefore, the issue becomes very important to make certain a suitable low pressure region in which one or more ionization means can achieve high ionization efficiency.

SUMMARY OF THE INVENTION

The current invention involves a method and an apparatus which provide high ionization and ion transmission efficiency in a low pressure region while at the same time maintain the convenience of direct analysis by desorbing samples under the ambient conditions.

The method involves forming gaseous neutral molecules directly from liquid/solid sample surface under atmospheric pressure near the inlet of an ion analyzer such as a mass spectrometer, transferring the gaseous neutral molecules into a low pressure region with pressure ranging from 10-14000 Pa, and ionizing the neutral gaseous molecules with a post-ionization means.

The means for generating ions from gaseous neutral molecules may include but not limited to low pressure ESI, vacuum UV photons, or a combination of both.

The apparatus described in the invention is composed of the following parts. Firstly, the apparatus contains a sample support for generating gaseous neutral molecules in the ambient conditions. The sample support may include a laser beam, a heated gas flow, a thermal heating plate, a plate vibrating at ultrasound frequency, or a thermal heating tube with the purpose of converting the samples in the condensed phase to neutral molecules in the gas phase. Secondly, the apparatus contains a transfer channel for effectively transporting the desorbed neutral molecules to a low pressure chamber. Thirdly, the apparatus contains a low pressure chamber where the neutral molecules are transferred to and are post-ionized. The low pressure chamber is maintained at a pressure between 10 to 14000 torr. Fourthly, the low pressure chamber contains a device with a time varying electric field which can guide and focus the ions immediately after they are generated. Finally, the apparatus contains a mass spectrometer, an ion mobility spectrometer, or a combination of both for analyzing the generated ions.

Due to using the technology described above, this invention has the following advantages compared to the currently available technology:

1. Rapid desorption under atmospheric pressure, efficient post-ionization in a designated pressure region;
2. A combination of two complimentary ionization methods in a designated pressure region; and
3. Efficient ion focusing and guiding in a designated pressure region after ionization.

DETAILED DESCRIPTION OF THE INVENTION

This invention proposed a method and an apparatus which can desorb samples under ambient conditions, convert solid samples into gas phase neutral molecules, transfer gas phase molecules into low pressure region and finally ionize these molecules in this low pressure region.

In the embodiments of the invention, the method of generating neutral molecules can be beyond those using laser, hot gas, or ultrasonic vibration.

In addition, this invention proposed a method and an apparatus which can generate gaseous neutral molecules from liquid chromatograph or similar devices, transfer gas phase molecules into low pressure region and finally ionize these molecules in this low pressure region.

In addition, this invention proposed a method and an apparatus which can generate gaseous neutral molecules from gas chromatograph or similar devices, transfer gas phase molecules into low pressure region and finally ionize these molecules in this low pressure region.

In the embodiment of the invention, the ionization methods can include but not limited to low pressure electrospray (LP-ESI), vacuum UV (VUV) photoionization, or a combination of the two. Specifically, the ionization process can happen through the interaction of the neutral molecules and the charged droplets from the LP-ESI or photons from the VUV source. Once the ions are generated in the low pressure region, they can be efficiently focused by an alternating electrical field, thus reducing the ion loss to the least extent.

One of the goals of the multiple embodiments of the invention is to increase the sensitivity of the ion source. This is mainly achieved by transferring neutral molecules at the interface of the atmospheric and low pressure regions instead of transferring ions, and also by focusing and guiding those generated ions in a low pressure region (10-14000 Pa) instead of in the atmospheric pressure. Combining the two secondary ionization methods (LP-ESI and VUV ionization) can further increase the number of types of the analytes that are ionizable. For the process of VUV ionization this pressure range is low enough for allowing VUV photons to reach the gaseous analytes, (vacuum UV photons are strongly absorbed by oxygen), but also maintain enough concentration of reactant ions from the background. To the process of the LP-ESI, this pressure range can reduce the ion loss at the ion transfer interface and in the mean time it is high enough for not freezing the solvent. In one or multiple embodiments of the invention, the device for analyzing the generated ions can be mass spectrometer or ion mobility spectrometer. The detailed embodiments are described as follows.

Figure 1:
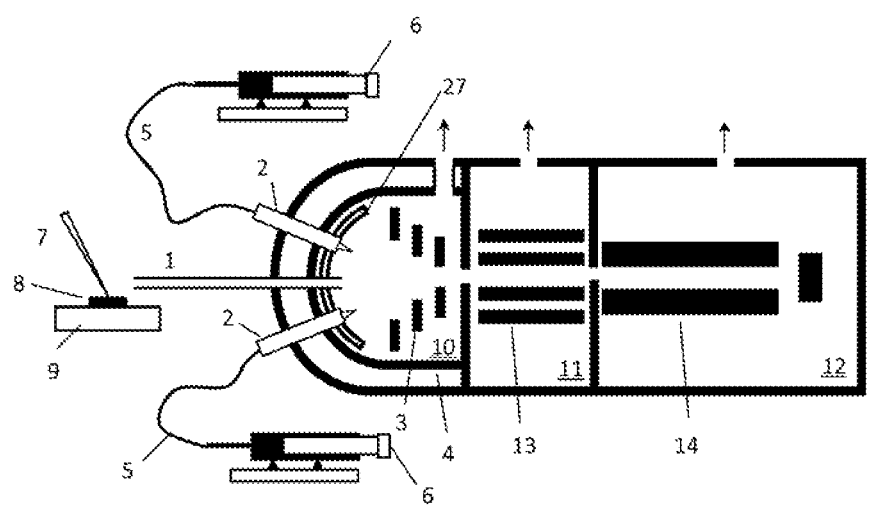
FIG. 1 is a schematic view of an apparatus according to a first embodiment of the invention.

FIG. 1 shows the first embodiment of the invention. The purpose of this embodiment is to perform sample desorption in the atmospheric pressure, LP-ESI, and mass analysis of the generated ions. In this embodiment solid sample 8 is placed on a sample substrate 9 located outside the vacuum and is subject to desorption by a beam of laser 7. As an alternative, the desorption process can also be achieved by means such as hot gas or ultrasonic vibration. The desorbed sample molecules are then transferred into a low pressure chamber 10 where the gaseous neutral molecules wound encounter a sprayed mist from the tip of a low pressure ESI probe 2. The solvent used for the LP ESI is provided by the syringe pump 5 and is introduced by the capillary 6. The pressure in the low pressure chamber 10 is preferred to be between 10 to 14000 Pa. The ESI probe 2 used here is preferred to be a nanospray probe where the i.d. of the spray capillary is preferred to be smaller than 10 micron and the flow rate is preferred to be less than 300 μL/min. During the encounter of the gaseous neutral molecules with the sprayed mist, the molecules would fuse into the droplets in the mist. The droplets containing the analyte molecules will then go through a desolvation step to leave behind the analyte ions with multiple charges. This post-ionization process is very similar to that in ELDI where the only difference is that the fusion step happens in the atmospheric pressure instead in the latter case. In the current embodiment, the method in the current invention has higher sensitivity due to higher transmission efficiency of the inlet capillary 1 for gaseous neutral molecules compared with for droplets. If the pressure in the first chamber is too low, the solvent around the ESI tip will evaporate and freeze very rapidly. Therefore, the ESI process will be affected.

Since gas exiting the inlet capillary 1 and entering the low pressure region 10 is subject to supersonic expansion and therefore a radial spread of the molecule stream, multiple ESI probes can be mounted around the inlet capillary 1, namely inlet for the neutral molecules, with a certain diameter as shown in FIG. 1, for the purpose of increasing the interaction between the sprayed mist and the desorbed neutral molecules.

An array of ion focusing plates 3 (FIG. 1 and FIG. 5) with shrunk inscribed diameters is located in the first chamber 10 and faces the end of the inlet capillary 1. In order to focus ions, each set of the plates 3 contains four electrodes and each pair of facing electrodes is supplied with the RF voltages of same phase and amplitude and the RF voltages supplied on the two pairs of the same set have same amplitude but opposite phase. Once the ions are generated in the first chamber 10, they will be confined by the RF field and moved towards the central axis of the RF region and at the same time will migrate towards the exit of the confinement field by a DC gradient formed by the array of the focusing plates 3 (by superimposing DC voltages on the plates). A DC potential with the same polarity as the target analyte ions is also applied on the curved shape electrode 27 in order to focus the ions towards the central axis of the first chamber 10. The ions exiting the first chamber 10 will then go through a second chamber 11 (preferred to be operated around 1 Pa) where an octapole 13 focusing device is used for further transferring and focusing ions. Finally the ions exiting the second chamber will enter the third chamber 12 and be subject to mass analysis by a quadrupole mass analyzer 14. In this embodiment, an ion funnel can be used to serve the same purpose of the array of ion focusing plates.

Figure 2:
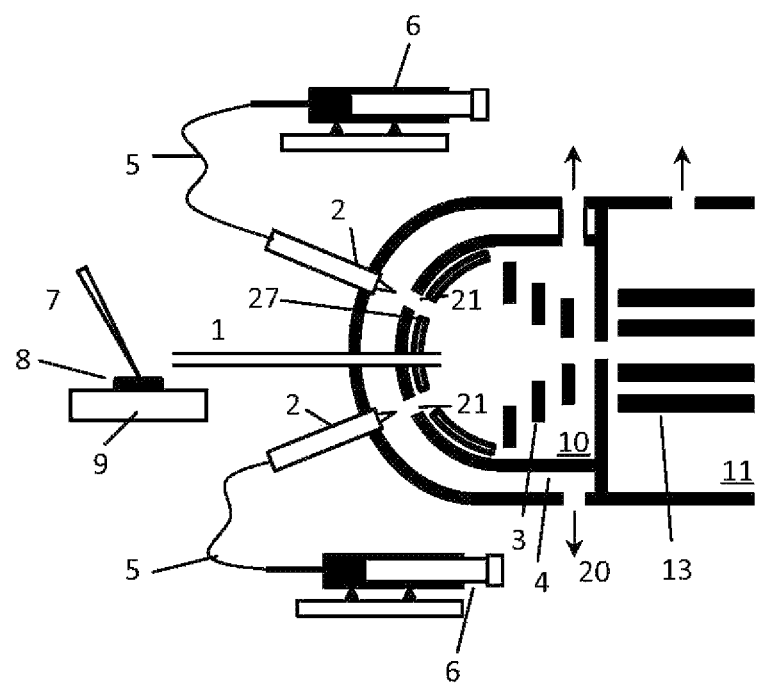
FIG. 2 is a schematic view of a source region of an apparatus as a variation of the apparatus described in the first embodiment.

As shown in FIG. 2 the ESI probe 2 tip can also recess to a hollow layer 4 between the outer wall and inner wall of the first chamber 10. The pressure in the hollow layer 4 can be adjusted through the pumping port 20. In this mode sprayed mist can be formed in the hollow layer 4 and then penetrate into the first chamber 10 through a small aperture 21. This hollow layer 4 can be maintained at a pressure different from that in the first chamber 10. For those solvents with high volatility, higher pressure than the pressure in the first chamber 10 is preferred to be used so that less freezing and boiling effects would result; whereas for solvents with low volatility, lower pressure than the pressure in the first chamber 10 is preferred to be used to generate droplets more efficiently with being capable of applying higher spray voltages.

Figure 3:
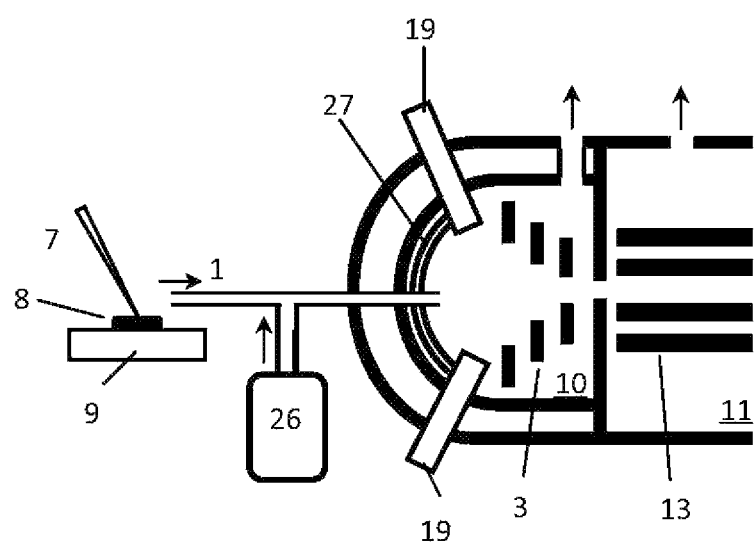
FIG. 3 is a schematic view of a source region of an apparatus according to a second embodiment of the invention.

The second embodiment of the current invention includes post-ionizing the desorbed molecules by a vacuum UV source 19 in the first chamber 10 as shown by FIG. 3. Similar to the first embodiment of the invention, the solid sample 8 placed on a sample substrate 9 can be laser desorbed into gas phase. The desorbed gaseous molecules are then transferred to the first chamber 10 where they are photoionized by photons from a vacuum UV source 19. The energy of the photons from the vacuum UV source 19 is preferred to be in the range from 8.4 to 11.8 eV, depending upon the type of analytes interested and the selectivity required. The vacuum UV source used can be a discharge lamp, an electron beam excited rare gas emission lamp source (EBELs), or a vacuum UV laser. Compared to atmospheric pressure photoionization (APPI) technique, ionization in the low pressure range by vacuum UV photons has higher efficiency since the strong absorption of the vacuum UV by ambient air will be minimized. Similar to the first embodiment, multiple VUV sources can be mounted around the inlet capillary 1 with a certain diameter in the first chamber 10 so that more photons can be provided to improve the ionization efficiency.

Figure 4:
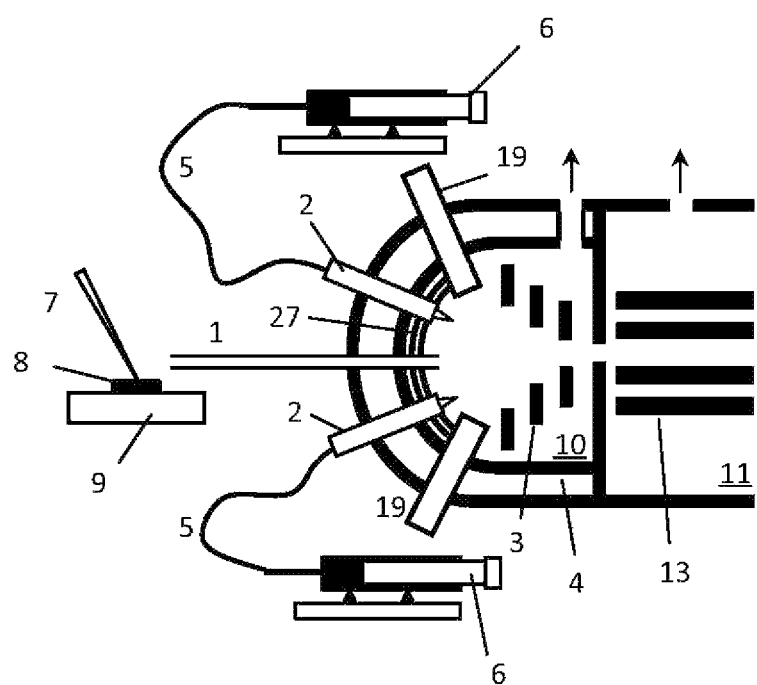
FIG. 4 is a schematic view of a source region of an apparatus according to a third embodiment of the invention.
Figure 5:
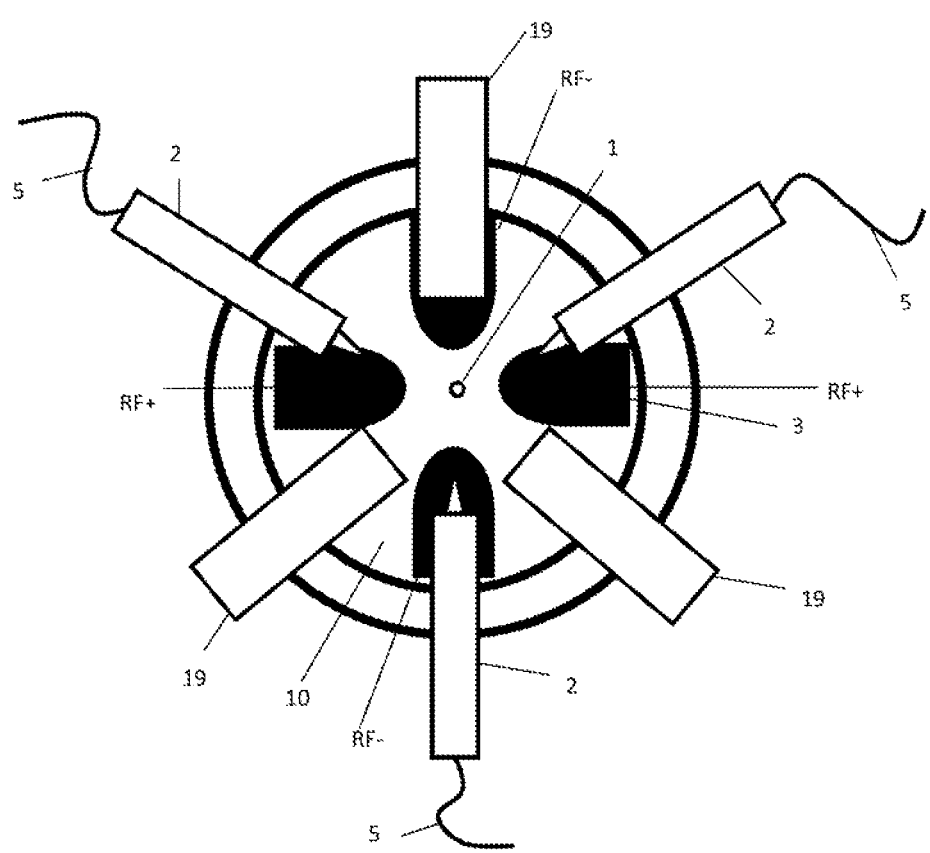
FIG. 5 is a front view of the source region shown in FIG. 3.

For those analytes with high ionization energy, the photon energy of the vacuum UV may still not be enough. Therefore occasionally the post-ionization of analytes will rely on a charge transfer process with the assistance of dopant ions. As shown in FIG. 3, the dopant gas from the dopant gas container 26 can be brought into the first chamber 10 along with the desorbed analyte molecules and ambient air molecules. The intermediate pressure used in the first chamber 10 of the current invention is advantageous since dopant molecules can still exist in it with a relatively high concentration while keeping a long path length for the VUV photons. Note that the dopant gas from the dopant gas container 26 will enter the first chamber 10 together with the desorbed analyte molecules, the number of the dopant gas molecules is estimated to be counted for half of the gas molecules in the first chamber 10, namely there are about $10^{13}/cm^3$ dopant molecules at the pressure of 130 Pa. The third embodiment of the current invention involves combining the two post-ionization methods mentioned above (LP-ESI and VUV) together as shown in FIG. 4. In this case the LP-ESI and the VUV source can be operated simultaneously in the first chamber 10 for ionizing the desorbed gaseous neutral molecules. As mentioned in the background of this invention the ESI and VUV are the two complementary techniques for ionizing either polar or non-polar species. This is particularly useful for analyzing samples from a complex mixture where analytes with different chemical properties exist. As mentioned in the previous embodiments, it is preferred to use multiple ESI probes 2 and VUV sources 19 in order to increase the chance for interaction between the neutral analytes and the droplets/photons. FIG. 5 shows the front view of the arrangement of multiple ESI probes 2 and VUV sources 19 where three ESI probes and 3 VUV sources circle around the inlet capillary 1. Many of other configurations of the ESI probes 2 and VUV sources 19 should work as long as the sprayed mist and the photons can interact with the neutral analytes exiting from the inlet capillary 1 in the first chamber 10.

Figure 6:
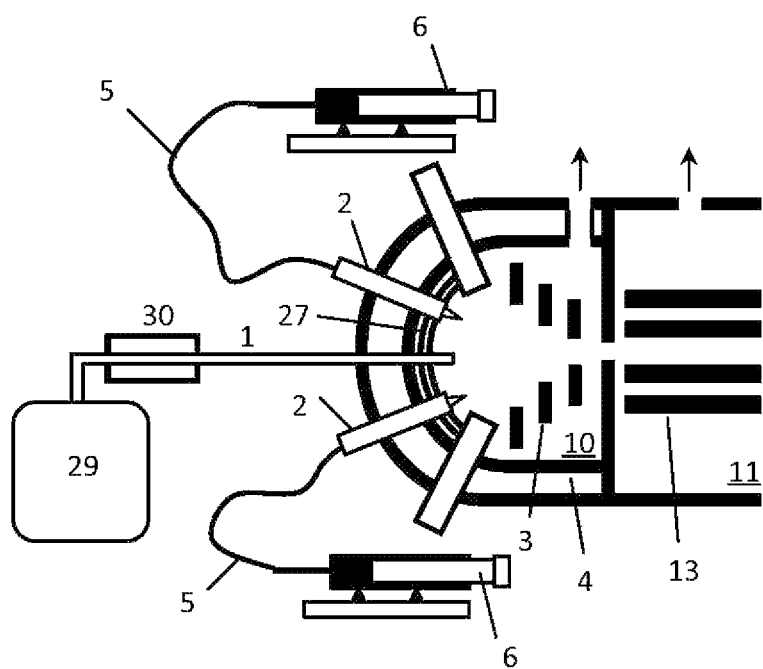
FIG. 6 is a schematic view of a source region of an apparatus according to a fifth embodiment of the invention.

The fourth embodiment of the current invention involves directly coupling the inlet capillary 1 of the first chamber 10 with a gas or liquid source. In this case the desorption source is replaced with a nano-LC 29 where the liquid analytes from within can enter the first chamber 10 through the heated transfer line 30 (FIG. 6). The purpose of using the heated transfer line is to vaporize the LC effluents so that the neutral gas molecules can be obtained in the first chamber 10. For those effluents that are difficult to evaporate, one can also use photo irradiation, ultrasonic vibration, or high flow of hot gas to generate neutral molecules in the ambient air. In this embodiment both ionization means can also be used at the same time. In the mean time, a gas chromatograph or a reaction chamber can be directly connected to the capillary inlet 1 where the exit of the gas inlet can be considered as the sample stage. The only difference between the interface of GC/reaction chamber and that of LC is that the former do not need a heated transfer line 30 for vaporization of the samples.

Figure 7:
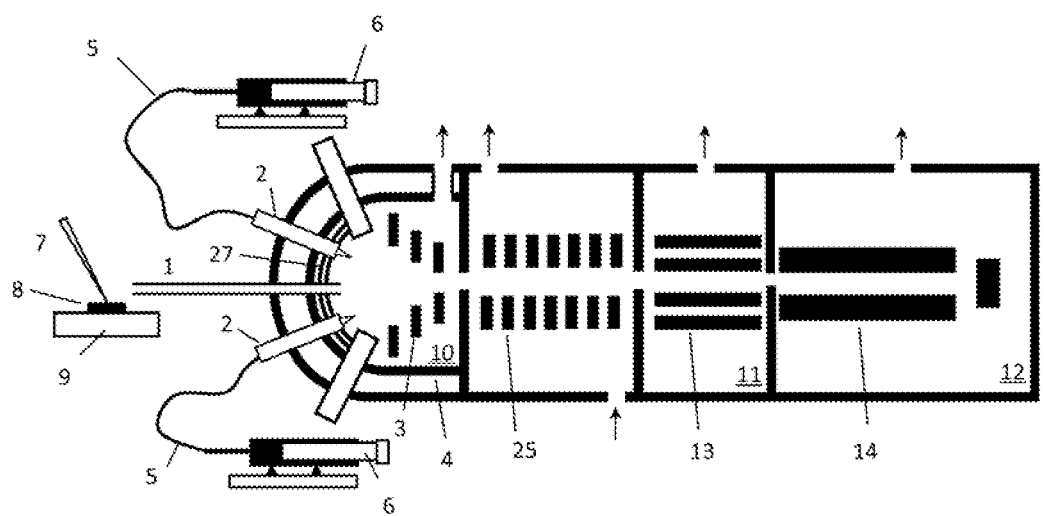
FIG. 7 is a schematic view of an apparatus according to a sixth embodiment of the invention.

The fifth embodiment of the current invention takes the same form of desorption and ionization as the previous four embodiments. The difference here is that ions exiting the first chamber 10 will enter a chamber which contains an ion mobility drift cell 25 as shown in FIG. 7. The drift cell can be operated substantially in the same pressure range as that of the first chamber 10 as long as the pressure is higher than 65 Pa. Ions will be driven forward by a DC gradient in the drift cell and later be analyzed by an mass analyzer.

It should also be seen that variations and modifications of the present invention additional to the embodiments described herein are within the spirit of the invention and the scope of the claims. For example, the gaseous neutral molecules can be from heating the effluents of a capillary electrophoresis device; the desorption source can be not only a laser beam or a heated gas flow, but also a heating lamp; the post-ionization source can be a glow discharge source or a radioactive source. Moreover, the advantages of combining the low pressure ESI and VUV can also be demonstrated by spraying the analytes directly with a LP-ESI probe and using VUV as a complimentary method for post-ionization.

What is claimed is:

1. A method for generating and analyzing ions, comprising:
   generating gaseous neutral molecules in an atmospheric pressure region outside a low pressure chamber;
   transferring said gaseous neutral molecules from said atmospheric pressure region outside said low pressure chamber into a first low pressure region in said low pressure chamber with a pressure range between 10 and 14000 Pa;
   generating ions from said gaseous neutral molecules in said first low pressure region; and
   focusing and guiding said ions with a time-varying electric field in said first low pressure region towards an ion analyzer.

2. The method as claimed in claim 1, wherein said gaseous neutral molecules are generated from a solid surface by desorption.

3. The method as claimed in claim 2, wherein said desorption for generating gaseous neutral molecules from solid surface includes desorption caused by irradiation of a laser beam, or by a heated gas flow.

4. The method as claimed in claim 3, wherein said step of desorption includes placing said solid sample onto a movable sample stage and moving the sample stage so that the laser beam is scanned across said solid surface to obtain information of spatial distribution of sample composition.

5. The method as claimed in claim 1, wherein said gaseous neutral molecules are generated from effluents of a liquid chromatograph by a vaporization means, or supplied by a gas chromatograph, or by a chemical reactor directly.

6. The method as claimed in claim 5, wherein said vaporization means includes heating by hot gas flow, light irradiation or ultrasonic vibration.

7. The method as claimed in claim 1, wherein said step of generating ions includes creating electrospray in said first low pressure region, and letting the gaseous neutral molecules fuse with the charged droplets from the electrospray inside said first low pressure region.

8. The method as claimed in claim 7, wherein said electrospray is nanoSpray.

9. The method as claimed in claim 1, wherein said step of generating ions includes fusing the gaseous neutral molecules with the charged droplets in said first low pressure region while the charged droplets are generated from a electrospray located in a second low pressure region with gas pressure being different from the pressure of the first said low pressure region.

10. The method as claimed in claim 9, wherein said second low pressure region has a pressure substantially higher or lower than that in said first low pressure region.

11. The method as claimed in claim 1, wherein said step of generating ions includes irradiating the neutral gaseous molecules with photons from a vacuum UV source in said first low pressure region.

12. The method as claimed in claim 1, wherein said ions are generated in said first low pressure region by interaction with both the charged droplets from said low pressure ESI probe and the photons from said vacuum UV source simultaneously.

13. The method as claimed in claim 1, wherein a DC field with an axial gradient is superimposed on said time varying electric field to drive said ions towards the exit of said first low pressure region.

14. The method as claimed in claim 1, wherein said ion analyzer includes a mass spectrometer or an ion mobility spectrometer.

15. An apparatus for generating and analyzing ions, comprising:
   a sample support located in an atmospheric pressure region where gaseous neutral molecules from a sample are generated;
   a transfer channel for transferring said gaseous neutral molecules;
   a first low pressure chamber, connected with the transfer channel, with pressure ranging from 10 to 14,000 Pa in which said gaseous neutral molecules are ionized; and
   a device generating time varying electric field in said first low pressure chamber for guiding and focusing said ions towards an ion analyzer for further analyzing said ions;
   wherein said atmospheric pressure region is outside said first low pressure chamber, and wherein the transfer channel transfers the gaseous neutral molecules from said atmospheric pressure region into said low pressure chamber.

16. The apparatus as claimed in claim 15, wherein said sample support includes a movable solid sample stage.

17. The apparatus as claimed in claim 16, including a laser to desorb the sample and generate said gaseous neutral molecules.

18. The apparatus as claimed in claim 17, wherein an irradiation spot of a laser beam emitted by the laser is scanned across said sample surface by moving said movable solid sample stage to obtain imaging information of the sample.

19. The apparatus as claimed in claim 16, including a hot gas flow generating device for thermo desorption and generating said gaseous neutral molecules.

20. The apparatus as claimed in claim 15, wherein said sample support includes an outlet of a liquid infusion device.

21. The apparatus as claimed in claim 20, wherein said liquid infusion device includes a liquid chromatograph or a capillary electrophoresis device.

22. The apparatus as claimed in claim 15, wherein the sample support includes an outlet of a gas infusion device.

23. The apparatus as claimed in claim 22, wherein the gas infusion device includes a gas chromatograph or a chemical reactor.

24. The apparatus as claimed in claim 15, including a low pressure electrospray probe having at least its front tip part within said first low pressure chamber, wherein said gaseous neutral molecules are ionized by fusing with charged droplets from the low pressure electrospray probe.

25. The apparatus as claimed in claim 24, including multiple low pressure electrospray probes, wherein the tips of the electrospray probes are positioned around the entrance of the gaseous neutral molecules in said first low pressure chamber.

26. The apparatus as claimed in claim 24, wherein said low pressure electrospray tip is a nanoSpray tip.

27. The apparatus as claimed in claim 15, including a second low pressure chamber with gas pressure different from that of said first low pressure chamber and in communicating with said first low pressure chamber with holes, wherein each tip of a low pressure electrospray probes is located in said second low pressure chamber, and points at the center of said first low pressure chamber through said holes.

28. The apparatus as claimed in claim 27, wherein the gas pressure of said second chamber is substantially higher or lower than that in said first chamber.

29. The apparatus as claimed in claim 15, including a vacuum UV source located in said first low pressure chamber for generating ions by irradiating said gaseous neutral molecules with photons from said vacuum UV source.

30. The apparatus as claimed in claim 29, including multiple vacuum UV sources positioned around the entrance of the gaseous neutral molecules in said first low pressure chamber, with a preset radius.

31. The apparatus as claimed in claim 30, wherein said vacuum UV source is a discharge lamp, a UV laser or a synchrotron radiation source.

32. The apparatus as claimed in claim 15, including a low pressure electrospray probe and a vacuum UV source both positioned in said first low pressure chamber, wherein the gaseous neutral molecules are ionized by interacting with both charged droplets from said low pressure electrospray probe and photons from the vacuum UV source.

33. The apparatus as claimed in claim 15, wherein said device generating time varying electric field for guiding and focusing ions include an ion focusing electrode array or an ion funnel.

34. The apparatus as claimed in claim 15, wherein said ion analyzer includes a mass spectrometer or ion mobility spectrometer.

* * * * *